United States Patent
Grooten et al.

(12) 
(10) Patent No.: US 6,344,192 B1
(45) Date of Patent: Feb. 5, 2002

(54) USE OF INTERLEUKIN-15

(75) Inventors: Johan Adriaan Marc Grooten, Lovendegem; Hans Peter Raf Dooms, Ypres; Walter Charles Fiers, Destelbergen, all of (BE)

(73) Assignee: Vlaams Interuniversitair Instituut voor Biotechnologie, Zwijnaarde (BE)

( * ) Notice: Subject to any disclaimer, the term of this patent is extended or adjusted under 35 U.S.C. 154(b) by 0 days.

(21) Appl. No.: 09/380,049

(22) PCT Filed: Feb. 23, 1998

(86) PCT No.: PCT/EP98/01127

§ 371 Date: Aug. 23, 1999

§ 102(e) Date: Aug. 23, 1999

(87) PCT Pub. No.: WO98/36768

PCT Pub. Date: Aug. 27, 1998

(30) Foreign Application Priority Data

Feb. 21, 1997 (EP) .............................................. 9720051

(51) Int. Cl.$^7$ .............................................. A61K 45/00
(52) U.S. Cl. .................... 424/85.2; 424/85.1; 435/69.5; 435/69.52; 435/386; 530/351; 930/140; 930/141
(58) Field of Search .............................. 424/85.2, 85.1; 435/69.52, 69.5, 386; 530/351; 930/140, 141

(56) References Cited

U.S. PATENT DOCUMENTS 5,574,138 A * 11/1996 Grabstein et al. ............ 530/351
5,698,194 A * 12/1997 Hadden ...................... 424/85.1
5,747,024 A * 5/1998 Grabstein et al. ........... 424/85.2

FOREIGN PATENT DOCUMENTS

WO  PCT/US95/05585  5/1995
WO  PCT/US96/16870  10/1996

OTHER PUBLICATIONS

Janeway C. Immunobiology, 2nd Ed. 1996, 1:16–1:18, 7:17 and 7:19,Garland Publishing Inc. New York.*

Moore G.J. Designing peptide mimetics, Trends in Protein Science. vol. 15 (1994) pp. 124–129.*

Juan Flo et al., Oral administration of a bacterical immunomodulator enhances the immune response to cholera toxin, *Vaccine*, vol. 14, No. 12, 1996, pp. 1167–1173.

Imtiaz A. Khan et al., IL–15 Augments CD8+ T Cell–Mediated Immunity Against *Toxoplasma gondii* Infection in Mice, *The American Association of Immunologists*, 1996, pp. 2103–2108.

Hirokazu Kanegane et al., Activation of Naive and Memory T Cells by Interleukin–15, *Blood*, vol. 88, No. 1, Jul. 1, 1996, pp. 230–235.

* cited by examiner

*Primary Examiner*—Jeffrey Stucker
*Assistant Examiner*—Ulrike Winkler
(74) *Attorney, Agent, or Firm*—Knobbe, Martens, Olson & Bear, LLP (57) ABSTRACT

The invention relates to the use of IL-15 or active variants thereof and/or IL-15 activity enhancing compounds for the manufacture of a pharmaceutical composition for manipulating memory cells of the immune system, such as manipulating viability ad/or responsiveness of said memory cells. The IL-15 activity enhancing compound is for example lipopolysaccharide (LPS). The invention further relates to the use of IL-15 inhibiting or eliminating compounds for the manufacture of a pharmaceutical composition for manipulating memory cells of the immune system. Such inhibiting or eliminating compounds are for example anti-IL-15 antibodies, anti-IL-15Rα antibodies, fragments of these antibodies, e.g. the Fab or F(ab')$_2$ fragment, soluble IL-15Rα, fusion proteins consisting of soluble IL-15Rα, and Fc fragment, compounds, e.g. peptides, binding and/or inhibiting functional IL-15 receptor, IL-15 antisense oligonucleotides.

7 Claims, 11 Drawing Sheets

USE OF INTERLEUKIN-15

RELATED APPLICATION

The present application is the U.S. national phase under 35 U.S.C §317 of International Application No. PCT/EP98/00127, filed Feb. 23, 1998.

BACKGROUND OF THE INVENTION

The present invention relates to a new use of Interleukin-15 (IL-15). The invention further relates to pharmaceutical preparations, containing IL-15 itself, IL-15 stimulating compounds or IL-15 inhibiting and/or eliminating compounds.

The cytokine interleukin-15 (IL-15) was originally identified in culture supernatants of the simian kidney epithelial cell line CV-1/EBNA and the T cell leukemia cell line HuT-102 (Grabstein et al., 1994; Burton et al., 1994; Bamford et al., 1994). The IL-15 cDNA sequence encodes a 162 amino acid (aa) precursor protein consisting of a 48 aa peptide and a 114 aa mature protein (Grabstein et al., 1994). Although there is no sequence homology with IL-2, analysis of the amino acid sequence predicts that IL-15, like IL-2, is a member of the four α helix bundle cytokine family. Furthermore IL-15 and IL-2 exert their biological activities through binding on the IL-2Rβ and γchains, supplemented by a specific IL-15Rα and IL-2Rα polypeptide, respectively (Giri et al., 1995). This sharing of receptor subunits probably accounts for the similar functional activities of both cytokines observed on T, B and NK cells. IL-15 mRNA is widely distributed in fibroblasts, epithelial cells and monocytes but not in resting or activated T cells, the predominant source of IL-2.

IL-15 and IL-2 share various biological functions. IL-15, like IL-2, has been defined as a T cell growth factor. IL-15 was originally discovered as a factor that could induce proliferation of the IL-2 dependent murine cytotoxic T-cell line (CD8$^+$) CTLL-2 (Grabstein et al., 1994). Proliferation upon addition with IL-15 was also observed in phytohaemagglutinin (PHA)-activated CD4$^+$ or CD8$^+$ human peripheral blood T lymphocytes (PBT), and γδ subsets of T cells (Grabstein et al., 1994; Nishimura et al., 1996). Studies with phenotypically memory (CD45RO$^+$) and naive (CD45RO$^-$) T cells, isolated from human PET, revealed that IL-15, like IL-2, induces in memory CD4$^+$ and CD8$^+$ T cells and naive CD8$^+$ T cells but not in naive CD4$^+$ T cells the expression of the CD69 activation marker and proliferation (Kanegane et al., 1996). IL-15 was as effective as IL-2 in the in vitro generation of alloantigen-specific cytotoxic T cells in mixed lymphocyte cultures and in promoting the induction of lymphokine activated killer (LAK) cells (Grabstein et al., 1994). Additionally, in vivo studies in a murine model demonstrated the capacity of IL-15 to augment CD8$^+$ T-cell-mediated immunity against *Toxoplasma gondii* infection (Khan and Kasper, 1996). Here vaccination of mice with soluble parasite antigen (Ag) and IL-15 resulted in significant proliferation of splenocytes expressing the CD8$^+$ phenotype and protection against a lethal parasite challenge for at least 1 month postimmunization.

Natural Killer (NK) cells are considered an important target for IL-15 action. Treatment of NK cells with IL-15 results in proliferation and enhancement of cytotoxic activity and in production of Interferon γ (IFNγ), tumor necrosis factor α (TNFα) and granulocyt-macrophage colony stimulating factor (GM-CSF) (Carson et al., 1994). Furthermore IL-15 can substitute for the bone marrow microenvironment during the maturation of murine NK1.1$^+$ cells from nonlytic to lytic effector cells (Puzanov et al., 1996).

Apart from its activities on T and NK cells, IL-15 costimulates, in a comparable way as IL-2, proliferation of B cells activated with immobilized anti-IgM or phorbol ester (Armitage et al., 1995). Stimulation of B cells with a combination of CD40L and IL-15 efficiently induces immunoglobulin synthesis. IL-15 has no stimulatory activity on resting B cells.

IL-15 was also found to have other biological activities. Chemoattractant factors are cytokines or chemokines that regulate the migration of lymphocytes to inflammation regions.

IL-15 is described as a chemoattractant factor for human PBT, inducing polarisation, invasion of collagen gels and redistribution of adhesion receptors (Wilkinson and Liew, 1995; Nieto et al., 1996). Murine mast cells proliferate in response to IL-15, but not to IL-2, using a novel receptor/signalling pathway, not shared with IL-2 (Tagaya et al., 1996). Furthermore, it has been shown that IL-15 and IL-2 have different effects on differentiation of bipotential T/NK progenitor cells, with IL-15 predominantly promoting the development of TCRγδ T cells and NK cells (Leclercq et al., 1996). The most striking difference, however, between IL-15 and IL-2 lies in their expression patterns. The presence of IL-15 mRNA in a variety of non-lymfoid tissues indicates that the secretion of the cytokine is not solely regulated by the immune system and/or that the cytokine can act outside the immune system itself. Accordingly, addition of IL-15 to a myoblast cell line affects parameters associated with skeletal muscle fiber hypertrophy, suggesting IL-15 has anabolic activities and increases skeletal muscle mass (Quinn et al., 1995).

Activated CD4$^+$ T lymphocytes play a key role in the development of an effective immune response against pathogens by providing the growth factors necessary for the expansion of the activated CD4$^+$ T lymphocytes (autocrine growth) and for the expansion of CD8$^+$ cytolytic cells and the differentiation of B cells into antibody-secreting plasma cells (paracrine "helper" activity).

After clearance of the pathogen, a subfraction of the generated Ag-specific T cells persist as memory cells, either in the lymphoid tissue or in the circulation. Throughout this application, "memory cells" are defined as antigen-experienced cells. These memory lymphocytes are small, resting cells which are optimally primed for the generation of a quantitatively and qualitatively superior, secondary response upon a re-encounter with the priming Ag. In order to accomplish the transition from activated CD4$^+$ effector cell to resting CD4$^+$ memory cell and to acquire long-term survival, these effectors need to acquire the following characteristics:

(i) being resistant towards, or escaping from, activation-induced cell death (AICD); AICD is responsible for attenuation of the immune reaction;

(ii) being independent from autocrine growth factors, produced during the immune response. Normally, the disappearance of these growth factors—a consequence of the ending of immune activity—results in growth factor depletion-induced cell death by apoptosis;

(iii) having the capacity, in case of a renewed contact with the antigen, to expand maximally by production of the necessary autocrine- and paracrine-acting helper cytokines such as IL-2.

SUMMARY OF THE INVENTION

The research that resulted in the present invention, indicated that IL-15 promotes the generation and persistence of CD4$^+$ memory cells, by promoting antigen activated CD4$^+$ T-lymphocytes to acquire the characteristics, mentioned above:resistance towards AICD, insensitivity towards apoptosis following growth factor withdrawal at the end of the antigen stimulus and high responsiveness towards renewed antigen challenge. Resistance towards AICD and insensitivity towards apoptosis determine the survival of the CD4$^+$T lymphocytes. Responsiveness is characterised by cell division, expansion of the cell number and production of helper cytokines.

Thus, treatment of antigen stimulated CD$^+$ cells with IL-15, even at very low concentrations, turns off the program of cell death running in the absence of growth factor. Unlike with IL-2, survival of CD4$^+$ T cells with IL-15 is not accompanied by DNA synthesis nor proliferation, demonstrating that IL-15 induces a resting phenotype in these cells. Moreover, the sensitivity towards AICD of CD4$^+$ T lymphocytes, cultured in presence of IL-2, is reversed by IL-15. Restimulation of these IL-15 treated, resting T cells with a suitable antigen (Ag) presented by Ag presenting cells (APC) results in maximal cell expansion, driven by a renewed production of helper cytokines. This cell expansion is not attenuated by a massive cell death as a consequence of AICD. In contrast to what is observed for cells cultured in presence of IL-2, the above-mentioned activities of IL-15 provide a method to achieve survival of immuno competent CD4$^+$ T lymphocytes, herewith strongly improving the secondary restimulation of CD4$^+$ T lymphocytes. In other words, the formation of immunological CD4$^+$ memory cells can be controlled in a positive sense, by an increased IL-15 activity, or in a negative sense, by a decreased IL-15 activity.

A first aspect of the present invention thus relates to the use of IL-15 in the manufacturing of a pharmaceutical preparation for the stimulation of the formation of memory cells. Such a stimulation can be used in a number of applications. It can be applied before, during or after vaccination to increase the efficiency of the vaccination against infection or diseases of which the pathological evolution derives, at least in part, from an inadequate CD4$^+$ T cell-dependent immune response. Thus, diseases, where the existence of sufficient numbers of Ag-specific CD4$^+$ memory cells is necessary to control (re-emergent) pathogens, are suitable indications for IL-15 treatment. Important but non-limiting examples of such pathogenic conditions are bacterial, parasitical or viral infections (e.g. HIV) and cancer.

Other possible indications of this approach are individuals showing hyporesponsiveness towards pathogens or vaccins, or suffering from a chronic infection or from a generally weakened immune condition. As we assume that the action of IL-15 becomes even more important towards the end of an acute immune response, promoting the subsequent quiescent period, therapeutic doses of IL-15 should preferentially be administered when the immune response is subsiding, in this way favouring the establishment and long-term survival of CD4$^+$ memory cells.

A second aspect of the present invention relates to those cases where an unwanted or harmful CD4$^+$ T cell-dependent immune response is (co-)responsible for disease. As an example, several reports demonstrated the involvement of autopathogenic CD4$^+$ T cells in autoimmune conditions. As a consequence it is anticipated that blocking the activity of IL-15 will suppress the long-term survival of autoreactive CD4$^+$ effector T cell clones as well as promote the regression of already formed autoreactive CD4$^+$ T cells, thus resulting in beneficial effects for patients suffering from an autoimmune condition. Therapy aiming at the inhibition of IL-15 activities can be accomplished by administration of agents interfering with the binding of IL-15 to its receptor such as antagonistic anti-IL-15 antibodies or anti-IL-15Rα antibodies or the Fab or F(ab')$_2$ fragments of these Ab, soluble IL-15Rα, fusion proteins consisting of soluble IL-15Rα and Fc fragment, or peptides binding with high affinity on the IL-15Rα without inducing signalling. A different approach consists of inhibiting IL-15 synthesis by administration of IL-15 antisense oligonucleotides through direct vaccination of patients with naked DNA, or by gene therapy approaches.

A third embodiment of the invention further relates to a pharmaceutical preparation promoting the formation of memory cells, which preparation contains IL-15 or IL-15 promoting compounds, possibly in presence of a suitable excipient. A fourth embodiment of the invention relates to a pharmaceutical preparation inhibiting the formation of memory cells, which preparation contains IL-15 inhibiting and/or eliminating compounds, such as IL-15 antibodies or compounds that interfere with the binding of IL-15 with its receptor, such as soluble IL15Rα, possibly in presence of a suitable excipient.

For the use of IL-15 according to the present invention, IL-15 can be administered by bolus injection, continuous infusion, sustained release from implants or other suitable technique. Administration may be by intravenous injection, subcutaneous injection, or parenteral or intraperitoneal infusion. IL-15 therapeutic agent will be administered in the form of a pharmaceutical composition comprising purified polypeptide in conjunction with physiologically acceptable carriers, excipients or diluents. Such carriers will be non-toxic to patients at the dosages and concentrations employed. Ordinarily, the preparation of such compositions entails combining a mammalian IL-15 polypeptide or derivative thereof with buffers, antioxidants such as ascorbic acid, low molecular weight (less than about 10 residues) polypeptides, proteins, amino acids, carbohydrates including glucose, sucrose or dextrans, chelating agents such as EDTA, glutathione and other stabilizers and excipients. Neutral buffered saline or saline mixed with conspecific serum albumin are exemplary appropriate diluents. Elevated levels of IL-15 can also be obtained by adoptive transfer of cells ex vivo transfected with constructs consisting of an IL-15 cDNA sequence driven by a potent promoter, or by introduction into the target cells of an IL-15 cDNA sequence after a suitable promoter.

The meaning of therapeutic in the present application is not limited to the treatment of an existing disease or condition, but comprises the use of IL-15 as support during vaccination and other profylactive treatments, where the formation of immunological memory cells is essential or helpful.

DETAILED DESCRIPTION OF THE INVENTION

The present invention can be executed with isolated IL-15. Suitable IL-15 sources are the culture medium of constitutively IL-15 producing human cell lines such as the T-102. Alternatively, recombinant IL-15 can be applied. WO 95/27722 gives the information needed to prepare recombinant IL-15. Recombinant IL-15 is commercial available as well. Alternatively, variants of IL-15 can be used, as long as they have the activity needed to stimulate the formation of memory cells. These variants are identified as "active variants". Active variants further comprise IL-15 fragments displaying sufficient IL-15 activity to be useful in the invention. Moreover, the activity of IL-15 can be stimulated in an indirect way by the addition of IL-15 inducing compounds, such as LPS for induction of IL-15 production in monocytes, or by IL-15 inducing methods, such as UVβ irradiation for keratinocytes.

For the second variant of the invention, isolated IL-15 inhibiting or eliminating compounds can be used. If these compounds are (poly)peptides, they may be produced by recombinant DNA techniques.

The present invention will be further elucidated with reference to the example below, which is only intended by way of explanation and does not imply any limitation whatever to the scope of the invention.

EXAMPLE

1. Materials and Methods 1.1. CD4+ T Cell Clone

The influenza A/H3 haemagglutinin (HA)-specific and H-2$^b$ restricted CD4+ murine T cell clone T-HA was developed in this laboratory by an initial immunisation of C57Bl/6 mice with 100 μg/ml bromelaïn cleaved haemagglutinin (BHA) and 0.5 mg/ml adjuvant (Ribi, Immunochem Research Inc., Hamilton, Mont., USA) and a second immunisation with 32 μg/ml BHA three weeks later.

5 days after this boost immunisation lymph nodes were isolated and $3.10^7$ cells were stimulated in vitro with 0.5 μg/ml BHA in 25 cm$^2$ culture flasks (Nunclon, Nunc, Roskilde, Denmark). On day 4 10 U/ml mouse IL-2 (from PMA stimulated EL4.IL-2 cells) was added to the cultures.

After 2 additional biweekly restimulations with 0.5 μg/ml BHA and APC, a pool of optimally HA-reactive T-lymphocytes was obtained. These T-HA cells were maintained long term in vitro by biweekly restimulation in 25 cm$^2$ culture flasks with 10 ng/ml BHA and $7 \times 10^7$ syngeneic spleen cells (3000 rad gamma irradiated). On day 2, 30 IU/ml rhIL-2 was added and T cells were further cultured and expanded by medium renewal and IL-2 addition every 4 days. C57Bl/6 mice (Broekman Instituut, Eindhoven, Netherlands) were used as a source of spleen cells. T-HA cells were cultured in 12.5 mM Hepes-buffered RPMI 1640 medium (Life Technologies, Paisley, Scotland) supplemented with 10% FCS (Life Science International), 2 mM Glutamax-I, penicillin/streptomycin, 1 mM sodium pyruvate (all from Life Technologies, Paisley, Scotland) and $5 \times 10^{-5}$ M 2-ME (BDH, Poole, England).

1.2. Cytokines

Recombinant human IL-2 (r-IL-2) had a specific activity of $1.3 \times 10^7$ IU/mg as determined in the CTLL-2 assay, hence 1 IU corresponds to 77 pg.

Recombinant human IL-15 (r-IL-15) was purchased from PeproTech (London, UK) and had a specific activity of $2 \times 10^6$ U/mg according to the manufacturer.

Hereafter, 'rIL-2' and 'IL-2', as well as 'r-IL-15' and 'IL-15' are are used interchangeably because it is not essential for the invention to use a recombinant form.

1.3. IL-2 or IL-15 Pretreatment

T-HA cells were harvested from cultures by incubation in non-enzymatic cell dissociation buffer (Sigma) and viable cells were separated from remaining irradiated spleen cells and dead cells by centrifugation on a Histopaque-1077 (Sigma, Irvine, UK) density gradient for 25 min at 2000 rpm. $2–5 \times 10^5$ T-HA cells were cultured for 48 h in 24-well flat-bottom tissue culture plates (Falcon) in the presence of variable concentrations of IL-2 or IL-15.

1.4. Proliferation Assays

Induction of proliferation by IL-2, IL-15 or Ag/APC was measured by incubating $1 \times 10^4$ T-HA cells with serial dilutions of IL-2, IL-15 or 200 ng/ml BHA and $2 \times 10^5$ irradiated C57B1/6 spleen cells as a source of APC in 96-well, flat-bottom, microtiter plates (Falcon 3072, Becton Dickinson, Franklin Lakes, N.J., USA). $^3$H-thymidine (Amersham) was added at 0.5 μCi/well for the last 8–12 h of the indicated incubation period. Cells were harvested on glass fiber filters and $^3$H-thymidine incorporation was measured on a Topcount betaplate counter (Packard). Results reported are means of triplicate cultures.

1.5. Cell-labelling with PKH2-GL

T-HA cells were harvested and washed twice in medium devoid of serum in polypropylene tubes. $1 \times 10^6–1 \times 10^7$ cells were resuspended in 1 ml diluent A and stained with 2 μM PKH2-GL (Sigma, St. Louis, Mo., USA) following the instructions of the manufacturer. Stained cells were washed twice with medium supplemented with 18% fetal calf serum (FCS) and incubated overnight in their culture medium to allow dissociation of excess dye from the membrane.

1.6. Analysis of Viable and Dead Cell Populations

Viable cell numbers were determined by counting trypan-blue dye excluding cells in a hemocytometer. Duplicate wells were always counted twice and results shown are averages of these 4 independent countings. Apoptosis was analysed by addition of 30 μM propidium iodide (PI) (ICN) to harvested cells and percentage of cells taking up PI was measured with an EPICS 753 flow-cytometer (Coulter Electronics, Luton, UK), equipped with an Argon ion laser emitting at 488 nm, after gating out cell debris. PI fluorescence was detected at 610–630 nm. Additionally, percentage of apoptotic cells was also determined by forward scatter analysis (results not shown). Data obtained by the latter method correlated well with the PI dye exclusion data.

In mixed cultures of PKH2-GL stained T-HA cells and APC splenocytes, numbers of viable and apoptotic T-HA cells were obtained by flow-cytometric analysis of PI-negative and -positive cells respectively that emitted green fluorescence (525 nm) from the PKH2-GL stain.

1.7. Antibodies and Reagents

For immunofluorescence, rat anti-mouse CD25 (clone PC 61) and rat anti-mouse CD71 (clone R217 17.1.3, kindly provided by Dr. G. Leclercq) were used as primary antibodies. Anti-CD25 and anti-CD71 binding was detected with a FITC-conjugated goat anti-rat IgG (Sera-Lab, Crawley Down, UK). The mitochondrial membrane potential was measured by addition of 1 μM Rhodamine123 (Molecular Probes Inc., Eugene, Oreg.) for 30 min to the cells and subsequent flow-cytometric analysis of the fluorescence intensity.

1.8. Cell Cycle Analysis

T-HA cells were harvested, washed once in cold PBS, and lysed in Krishan's reagent (0.05 mg/ml PI, 0.02 mg/ml ribonuclease A, 0.3% Nonidet P-40, 0.1% sodium citrate). Cell nuclei were analysed for DNA content by flow-cytometry. The distribution of cells along the distinct stages of the cell cycle was calculated with MDADS Paral software (Coulter Electronics).

1.9. Experiments with Freshly Isolated Spleen Cells $8 \times 10^8$ spleen cells were prepared from spleens of naive, 8 week old C57Bl/6 mice and were activated in 25 cm$^2$ tissue culture flasks (Falcon, Becton Dickinson) with 1 μg/ml soluble anti-CD3 mAb (145-2C11). After 24 h, excess antibody was removed and cells were further cultured for 72 h without addition of exogenous cytokine. Following this stimulation period, cultures were harvested and CD4$^+$ T cells were isolated by immunomagnetic cell sorting. A negative selection procedure, using an Ab cocktail designed for the enrichment of murine CD4$^+$ T cells (StemSep, Stem Cell Technologies, Vancouver, Canada), was followed according to the manufacturer's instructions. $7.5 \times 10^6$ recovered cells were further cultured for 10 days and supplemented (every fourth day) with their respective cytokines (no, 10 ng/ml IL-15 or 10 ng/ml IL-2). Viable cell numbers were determined on day 14 based on trypan blue dye exclusion. For restimulation 1 μg/ml soluble anti-CD3 mAb and the immortalized macrophage cell line Mf4/4 (freely available from De Smedt, Universiteit Gent) were used. Prior to use, Mf4/4 cells were activated for 24 h with 400 U/ml IFN-γ to enhance expression of costimulatory molecules. Then, they were treated for 90 min with 30 μg/ml Mitomycin-C (Duchefa, Haarlem, The Netherlands) in order to block their proliferation, thus avoiding interference with proliferation-measurements from the restimulated lymphocytes. Alternatively, for determination of susceptibility to anti-CD3-induced death, freshly isolated, unsorted spleen cells were activated for 72 h in 24-well plates with 1 μg/ml soluble anti-CD3 mAb (145-2C11) without exogenous cytokine and were supplemented on day 3 with 10 ng/ml IL-15 or IL-2. After an additional 8 day culture period, the cells were harvested and restimulated with plate-bound anti-CD3 mAb (10 μg/ml). Apoptotic cell numbers were determined after 24 h by PI dye uptake. CD4/CD8 ratios were determined by labeling $1 \times 10^5$ cells with 0.5 μg PE-conjugated rat anti-mouse CD4 mAb (Pharmingen, San Diego, Calif.) and 0.5 μg/ml FITC-labeled rat anti-mouse CD8 mAb (clone 53–6.7, kindly provided by Dr. G. Leclercq, Ghent, Belgium) and, after gating out dead cells and debris, analysis of stained populations on a FACScalibur flow cytometer (Becton-Dickinson). Absolute numbers of. CD4$^+$ T cells in the respective cultures were calculated from the percentages obtained and total viable cell countings by trypan-blue dye exclusion.

2. Results 2.1. IL-15 is a Survival Factor, Protecting CD4$^+$ T Cells Against Cell Death Following Growth Factor Withdrawal without Inducing Proliferation During the acute activation phase by antigen, CD4$^+$ effector cells transiently produce high levels of IL-2, resulting in autocrine growth and strong expansion of the lymphocytes. However, following termination of the effector phase and hence, the ending of cytokine production, the generated lymphocytes become dependent on the exogenous supply of growth factors, mainly IL-2, for their survival. We studied the survival of activated T-HA cells, harvested four days after stimulation with Ag/APC, in the presence of increasing concentrations of IL-2 or IL-15. After three days of treatment with different concentrations of cytokines, the uptake of $^3$H-thymidine as a measure for cell division, the absolute numbers of viable lymphocytes and the percentage apoptotic cells in the various cultures were determined (FIG. 1).

Figure 1:
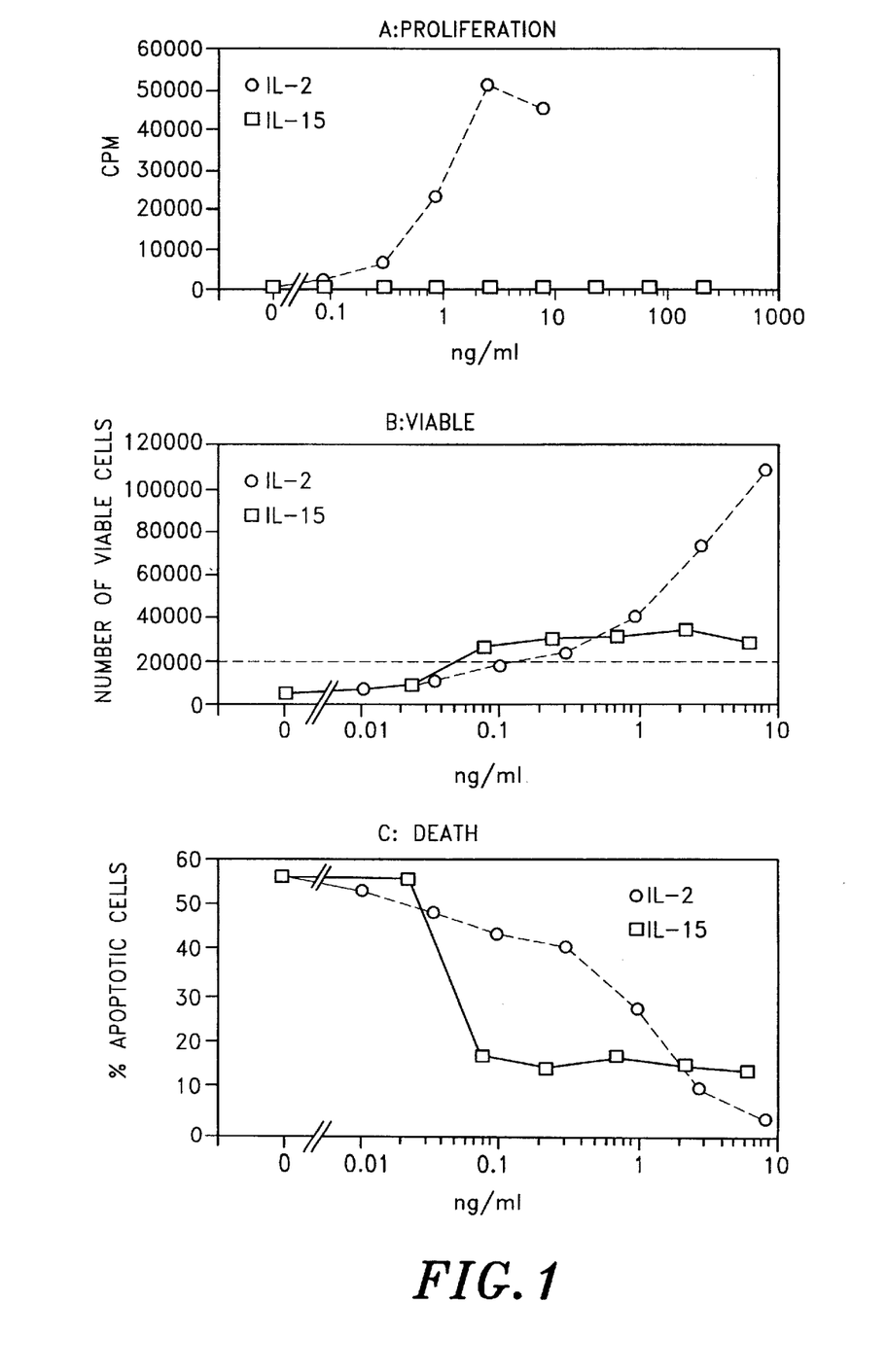
FIG. 1: IL-15 is mainly a survival factor, while IL-2 is mainly a proliferation-inducing factor.

In contrast to treatment with IL-2, treatment with IL-15 did not result in cell division (FIG. 1A). These results are in contrast with the results obtained by Kanegane & Tosato (1996), who claimed that CD4$^+$ cells proliferate upon addition of IL-15. This discrepancy is probably due to the presence of low amounts of IL-2 (besides IL-15) in their experiments. Unexpectedly, notwithstanding the absence of growth factor activity by IL-15, IL-15 treated T-HA lymphocytes showed protection towards cell death, normally occurring in absence of growth factor activity:the cell numbers remained unchanged at an IL-15 concentration of 0.1 ng/ml or higher (FIG. 1B) and no increase of the percentage of apoptotic cells was seen (FIG. 1C). This is in clear contrast with the explicit decrease of the number of viable cells and the corresponding increase of dead cells in absence of cytokine, a reflection of the growth factor depletion-induced cell death as well as with the cell growth-associated survival of IL-2 treated T-HA lymphocytes (FIG. 1).

From these data we conclude that IL-15, but not IL-2, is capable of inducing a survival signal in CD4$^+$ T lymphocytes without driving the cells into the proliferative cell cycle. In this way, IL-15 establishes a resting phenotype in T-HA lymphocytes that is linked, however, to survival. Moreover, under conditions of low cytokine concentration, in the range of 0.1 ng/ml, the net recovery of viable T-HA cells was considerably higher when cells were cultured with IL-15 instead of IL-2. Based on the preservation of viability in absence of active cell division upon IL-15 treatment, this example shows that the IL-15 polypeptide gives to the antigen is activated CD4$^+$ T lymphocytes the property to survive as a resting cell in absence of cytokine with inherent growth activity. In this way, IL-15 acts as a factor, enabling the survival of antigen-primed CD4$^+$ T lymphocytes, generated by a preceding antigenic activation, or resting cells.

2.2. IL-15Induces a Resting Phenotype

It is thought that after conclusion of a primary immune response a fraction of activated effector cells reverts to a resting state and persists in the animal as a population of small lymphocytes, ready for a "memory" response in case of re-emergence of their antigen. It was wondered whether T-HA lymphocytes surviving with IL-15 without cycling could be phenotyped as small, resting lymphocytes. Therefore a number of features generally recognized as parameters for lymphocyte quiescence were studied. It was determined whether the observed growth-arrest took place in a specific phase of the cell cycle. Cell cycle analysis by flow cytometry revealed that IL-15 treated cells accumulated in $G_0/G_1$ (FIG. 2), indicative of the induction by IL-15 of an arrest in cell cycle entry. Thus, cycling cells treated with IL-15 are neither arrested immediately nor randomly, which in fact would be apoptosis-inducing, but proceed with their cycle until they reach $G_0/G_1$ and then exit cell cycle progression in an orderly manner, i.e. without triggering programmed cell death.

Figure 2:
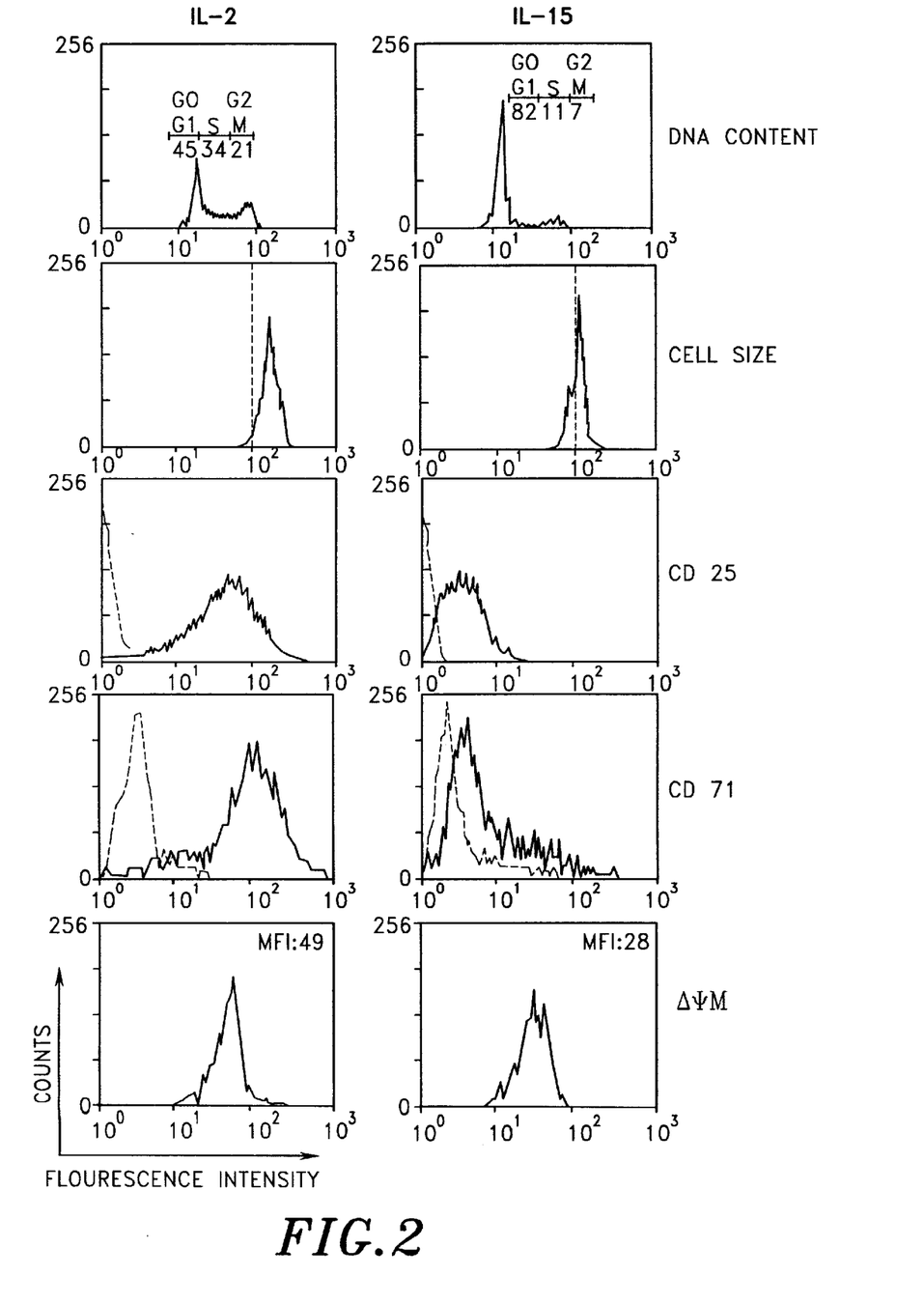
FIG. 2: IL-15 induces a resting phenotype.

Additionally, cell size, expression of activation markers and mitochondrial transmembrane potential ($\Delta\Psi_m$) as an indicator of the metabolic state of the cells were evaluated. IL-15-treated T-HA cells exhibited all the hallmarks of resting cells: the cells were small, expressed low levels of the CD25 (IL-2Rα) and CD71 (transferrin receptor) activation markers, and had a low $\Delta\Psi_m$ (FIG. 2). In contrast, IL-2-cultured cells were large blastoid cells with high CD25 and CD71 expression levels and a high oxidative metabolism as indicated by the increased $\Delta\Psi_m$. Thus, the IL-15-induced arrest in $G_0/G_1$ of T-HA cells is accompanied by acquisition of a typical quiescent phenotype.

2.3. IL-15 Protects the CD4$^+$ Helper T Cell Clone T-HA Against AICD

AICD of mature T-lymphocytes is generally considered as a key mechanism, restricting both the strength and duration of an immune response (Critchfield et al., 1995). It has been shown that clonal expansion and as a consequence, IL-2 is an important regulator of susceptibility to AICD as T lymphocytes cultured in the presence of IL-2 easily undergo apoptosis following crosslinking of the T-lymphocyte receptor for antigen (TCR) (Lenardo, 1991). We compared the influence of IL-2 and IL-15 treatment on responsiveness of T-HA cells towards stimulation by Ag/APC. T-HA cells were treated for 48 h with IL-15 (1 ng/ml) or IL-2 (100 IU/ml (7.7 ng/ml) or 1 IU/ml (0.077 ng/ml)) prior to antigenic restimulation.

Figure 3:
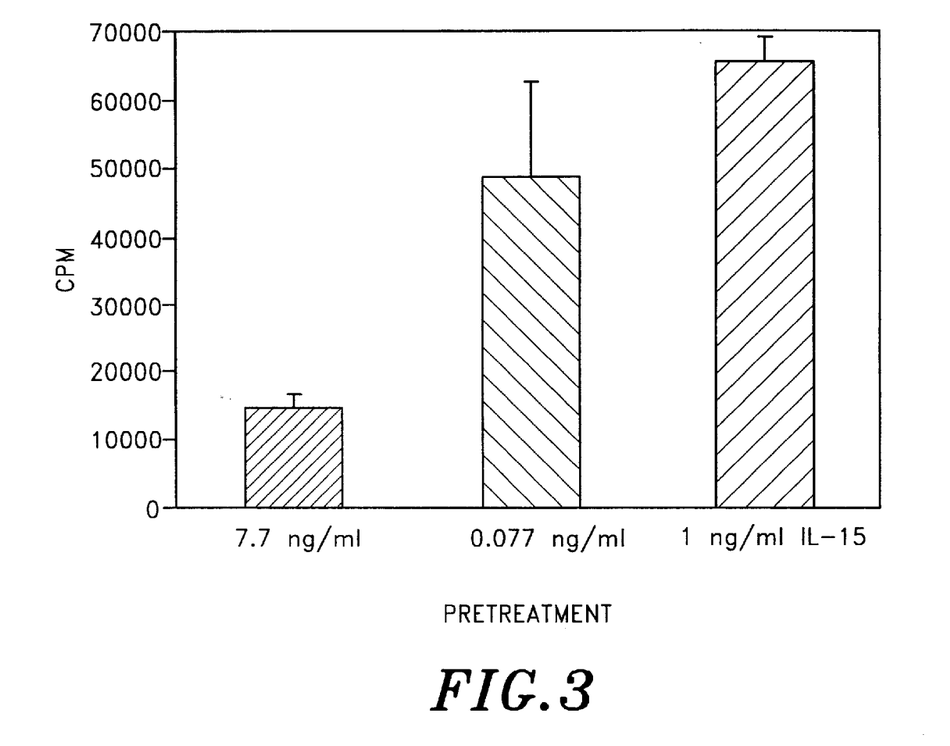
FIG. 3: IL-15 or low-dose IL-2 treated T-HA cells show increased proliferation in response to Ag/APC stimulation.

As was described above, cells differed functionally at the moment of restimulation according to the cytokine added: IL-15 kept the T-HA cells fully viable but non-proliferating, while high-dose IL-2 (7.7 ng/ml) induced vigorous cell cycling and treatment with low-dose IL-2 (0.077 ng/ml) resulted in extensive cell death. T-HA cells pretreated with IL-15 proliferated dramatically stronger in response to antigenic restimulation as compared to cells cultured in the presence of 100 IU IL-2 (FIG. 3). The small fraction of T-HA cells surviving incubation with 1 IU/ml IL-2, exhibited a reactivity towards Ag/APC similar to cells pretreated with IL-15.

In a next step we wanted to answer the question whether this differential responsiveness was a reflection of a differential sensitivity towards AICD or rather the consequence of differing proliferative capacities of IL-2 versus IL-15 pretreated cells. For this purpose, T-HA cells were labelled with a green fluorescent dye prior to Ag/APC stimulation, allowing them to be discriminated from APC present in these cultures during analysis of viable and dead cell numbers by flow cytometry.

Figure 4:
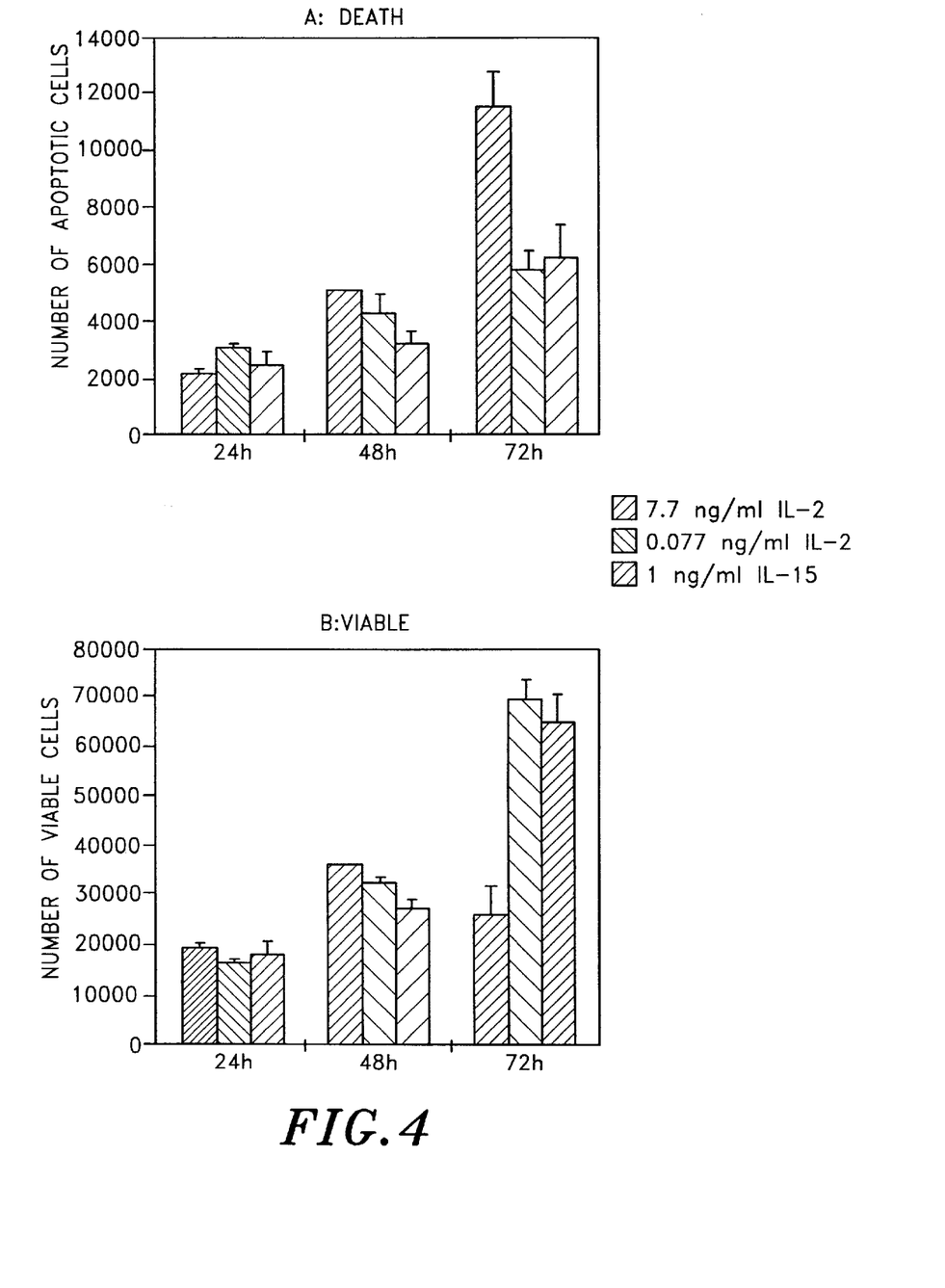
FIG. 4: IL-15 or low-dose IL-2 treatment of T-HA cells results in increased generation of effector cells during an Ag/APC response.

The results shown in FIG. 4A clearly demonstrate that the defective immune responsiveness observed with T-HA cells pretreated with 7.7 ng/ml IL-2 is the consequence of extensive cell death, apparent 48 h after start of the activation with Ag/APC. This is in agreement with the generally accepted view that IL-2 sensitizes T cells for AICD. On the contrary, T-HA cells cultered in the presence of IL-15 were efficiently protected against cell death occurring during antigenic activation, resulting in the generation of high numbers of effector cells (FIG. 4). Comparable results were obtained with the small population of T-HA cells surviving a low-dose 0.077 ng/ml IL-2 treatment. This result illustrates the inhibitory activity of IL-15 on Ag/APC induced cell death (AICD) and, as a result of this activity, the considerably increased formation of effector T-lymphocytes after a renewed, secondary stimulation with antigen of the IL-15 treated, resting CD4$^+$ T lymphocytes.

2.4. Protection by IL-15 Against AICD and Against Growth Factor Withdrawal-induced Apoptosis Strongly Potentiates Immune Responsiveness Upon Rechallenge with Antigen In this example, the effect of the IL-15 treatment on the strength of the secondary immune response of CD4$^+$ T lymphocytes is illustrated. T-HA lymphocytes were cultured in the presence of IL-15, or in high- or low-dose IL-2 before and after restimulation with Ag/APC.

Figure 5:
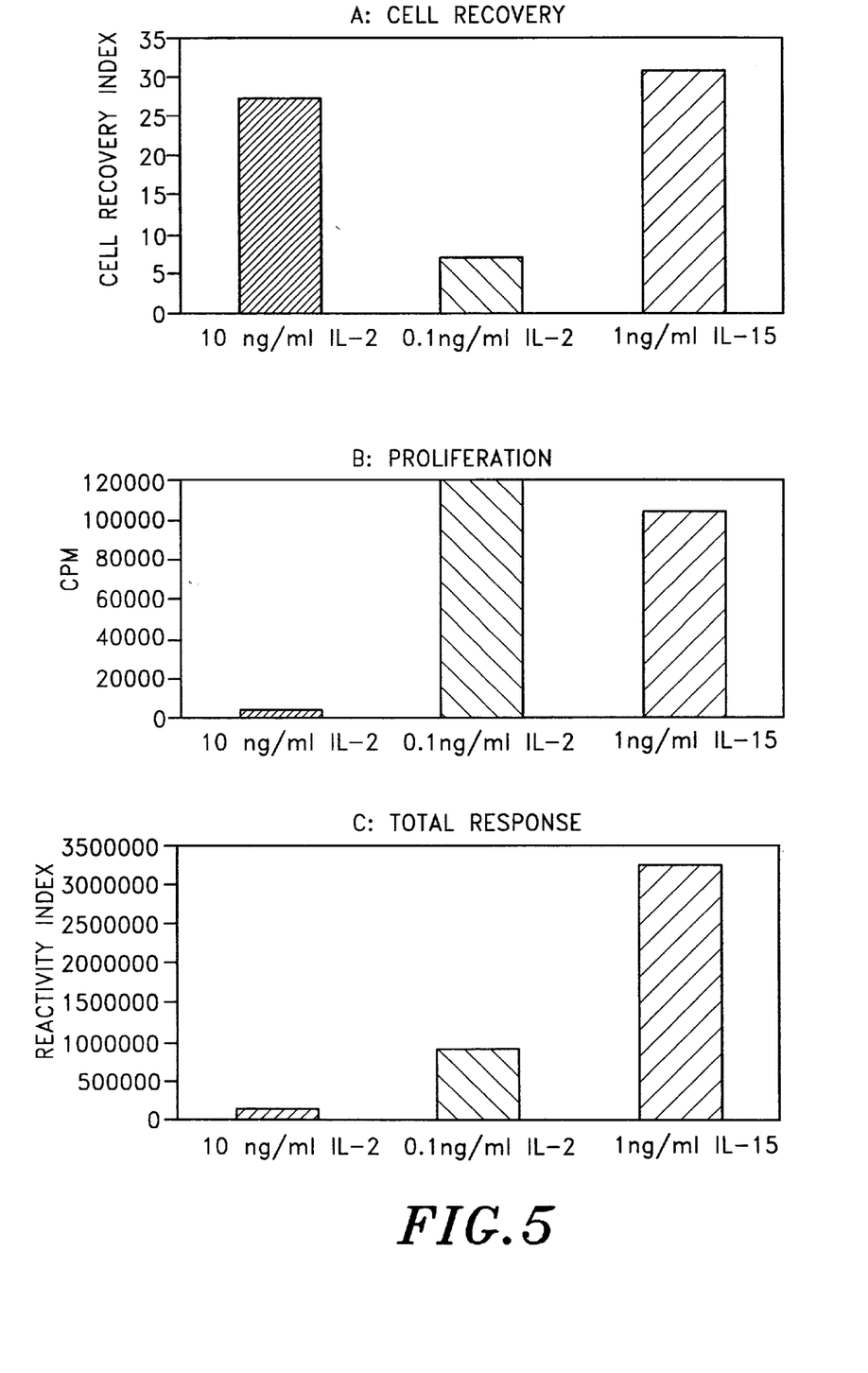
FIG. 5: Culture of T-HA cells in the presence of IL-15 results both in optimal recovery of cells after primary antigenic restimulation and in optimal proliferative responsiveness upon secondary antigenic restimulation.

As shown in FIG. 5A, the presence of IL-15 resulted in the preservation over a long time of the highest number of T-lymphocytes, generated in response to a preceeding antigenic stimulation. Thus, starting from a fixed number of IL-15 treated T-HA cells, the combination of optimal proliferation in response to Ag/APC stimulation and optimal persistence of the generated effector cells by addition of IL-15 after termination of the response to antigen, resulted in a 31-fold increase of T cells available for a second Ag/APC response. High-dose IL-2, sensitizing towards AICD, or low-dose IL-2, insufficiently supporting growth and viability, raised T cell numbers 27.3 and 6.7 fold respectively (FIG. 5A).

Figure 6:
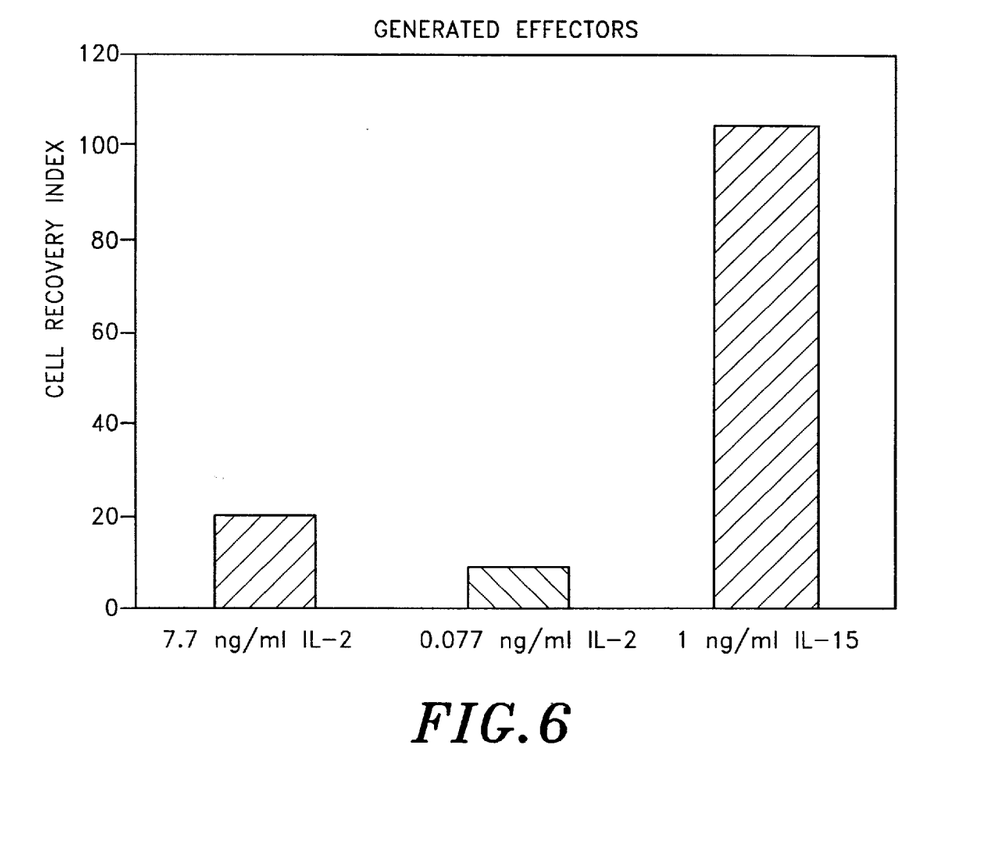
FIG. 6: Culture of T-HA cells in the presence of IL-15 results in strongly enhanced generation of immune effector cells.

T cells that survive with IL-15 remained optimally sensitive towards subsequent activation by antigen (FIG. 5B). The combination of a high yield of T lymphocytes after primary stimulation with antigen, optimal persistence and high reactivity upon renewed stimulation with antigen of IL-15 treated CD4$^+$ T lymphocytes resulted in a maximal reactivity index of the thus treated T-HA cells (FIG. 5C). Furthermore, the cumulative effect of this reactivity leads to a 105 fold yield in effector cells as shown in FIG. 6. T-HA lymphocytes that survive due to high or low doses of IL-2 generated a considerably weaker reactivity index (FIG. 5C) and, as a consequence, merely 20 and 8 fold increases in cell numbers, respectively, 3 days after secondary stimulation (FIG. 6).

Obviously, IL-15 both enhances the availability as well as the responsiveness of cells resulting in maximal secondary responses, features that cannot be achieved by any dose of IL-2. These results clearly demonstrate that IL-15, but not IL-2, possesses the properties necessary for generating an efficient immune memory, i.e. providing a strong survival signal allowing the persistence of immune effectors in a quiescent state and priming these memory cells for optimal response in case of renewed Ag stimulation by inducing insensitivity towards AICD. Taken together our study defines a unique novel pro-memory function for IL-15, clearly distinct from the physiological activities exerted by IL-2 or other cytokines with growth factor activity.

2.5. Induction of Quiescence and Protection Against Apoptosis by IL-15 Also Occurs with ex vivo Isolated T Cells Fresh, unsorted spleen cells from naive C57Bl/6 mice were isolated and polyclonally stimulated in vitro. The stimulus consisted of soluble anti-CD3 mAb (1 μg/ml) which, in the presence of costimulation by spleen APC, polyclonally activates naive T cells (Tamura, T., and Nariuchi, H., J. Immunol. 148:2370, 1992). After 24 h, remaining anti-CD3 mAb was removed and the activated cells were further cultures in the absence of exogenous cytokine. To confirm that activation occurred, anti-CD3 mAb-activated and unstimulated cells were pulsed with $^3$H-thymidine. Soluble anti-CD3 mAb induced a strong proliferative response: 25,304 cpm as opposed to 2,581 cpm for unstimulated cells. On day 4, CD4$^+$ cells were isolated by immunomagnetic cell sorting and further cultured without cytokine or in presence of IL-15 (1 ng/ml).

Figure 7:
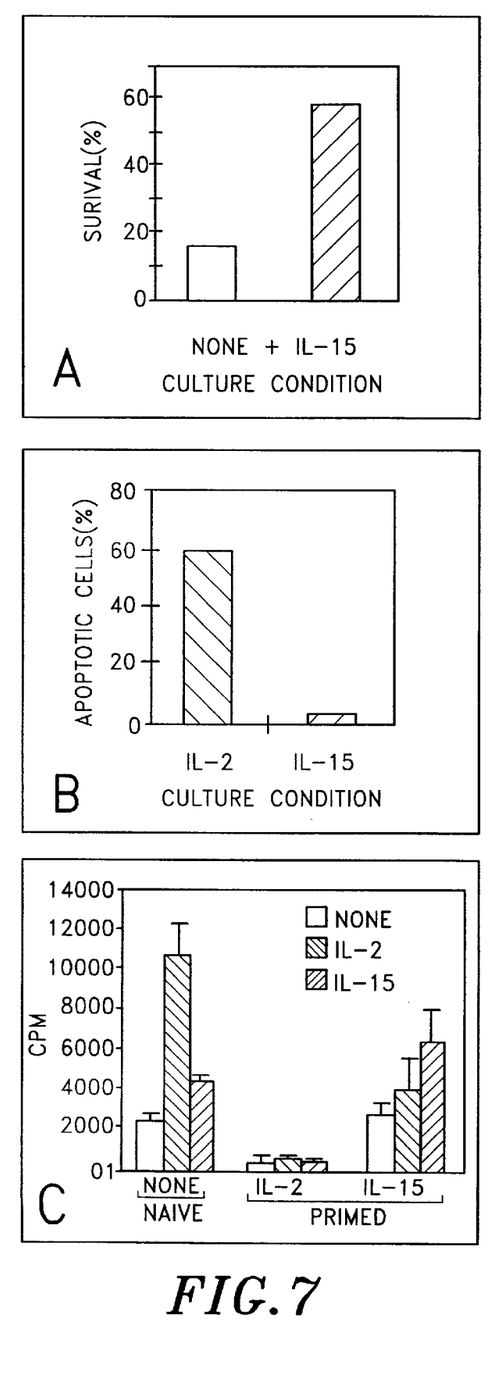
FIG. 7: IL-15 protects activated polyclonal CD4+ T cell populations against growth factor withdrawal-induced PCD and TCR-induced death.

After 10 days of culture in the absence of exogenous cytokine, viable cell numbers had dropped to 15% of the cell input, while IL-15 maintained cell numbers at approximately 60% of cell input (FIG. 7A). Cells surviving with IL-15 appeared as small resting lymphocytes and did not reveal DNA synthesis (59 cpm with 10 ng/ml IL-15) whereas proliferation could be induced with IL-2 (4,184 cpm with 10 ng/ml). Hence, also for freshly isolated and TCR-activated CD4+ T cells, IL-15 acts as a survival factor and induces quiescence.

Next, the resistance to TCR-induced cell death was investigated, triggered by immobilized anti-CD3 mAb, in these polyclonally activated T cell cultures. The CD4+ T cell population maintained throughout with IL-15 was largely resistant, whereas cells cultured with IL-2 showed extensive cell death (FIG. 7). Finally, CD4+ T cells residing in an IL-15-induced, resting state proliferated in response to renewed stimulation with soluble anti-CD3 and APC, while cells maintained with IL-2 did not (FIG. 7C). Also here, addition of IL-15 to the IL-15 pretreated cultures further increased the proliferative response, hence confirming the growth-promoting activity of IL-15 in the presence of TCR aggregation. These experiments demonstrate that the characteristics induced by IL-15 in the clonal CD4+ T cell T-HA namely long-term survival as a resting population, resistance to apoptosis and increased responsiveness to TCR restimulation, are also acquired by freshly isolated CD4+ T cells treated with IL-15.

2.6. In vivo Evaluation of the Capacity of IL-15 to Enhance Memory Responses

In vitro, the activities of IL-15 described here show that this cytokine is a factor promoting the generation and persistence of memory CD4+ T cells, thus enhancing secondary/memory immune responses to an antigen. It was investigated whether administration of IL-15 in vivo during and/or after a primary immune response against an antigen could enhance the secondary/memory response against this antigen.

Therefore IL-15 was delivered by a slow-release mini-osmotic pump or by bolus injections to mice immunized with haemaglutinnin (HA) and responsiveness to a renewed challenge with this antigen was evaluated. In the first experiment the initial immunisation consisted of two injections with HA: 5 µg injected intraperitoneal (IP) on day 0 and another 5 µg injected subcutaneous (SC) in the right flank on day 3. On day 4, a bolus injection of 1 µg hIL-15 in a volume of 100 µl PBS was given (or 100 µl PBS as a control). Two hours after this initial delivery, an ALZET mini-osmotic pump (model 2002, Alza Corp., Palo Alto, Calif.), filled with 10 µg hIL-15 in 235 (±5,7) µl PBS or with PBS without cytokine, was implanted SC on the back of the mouse. The opening of the pump was oriented towards the place where the SC injection of HA was given. Filling of the pump was performed according to the manufacturer's instructions. The pumps released IL-15 in the animal at a flow rate of 0,52 (±0,03) µl/hr during 14 days.

Figure 8A:
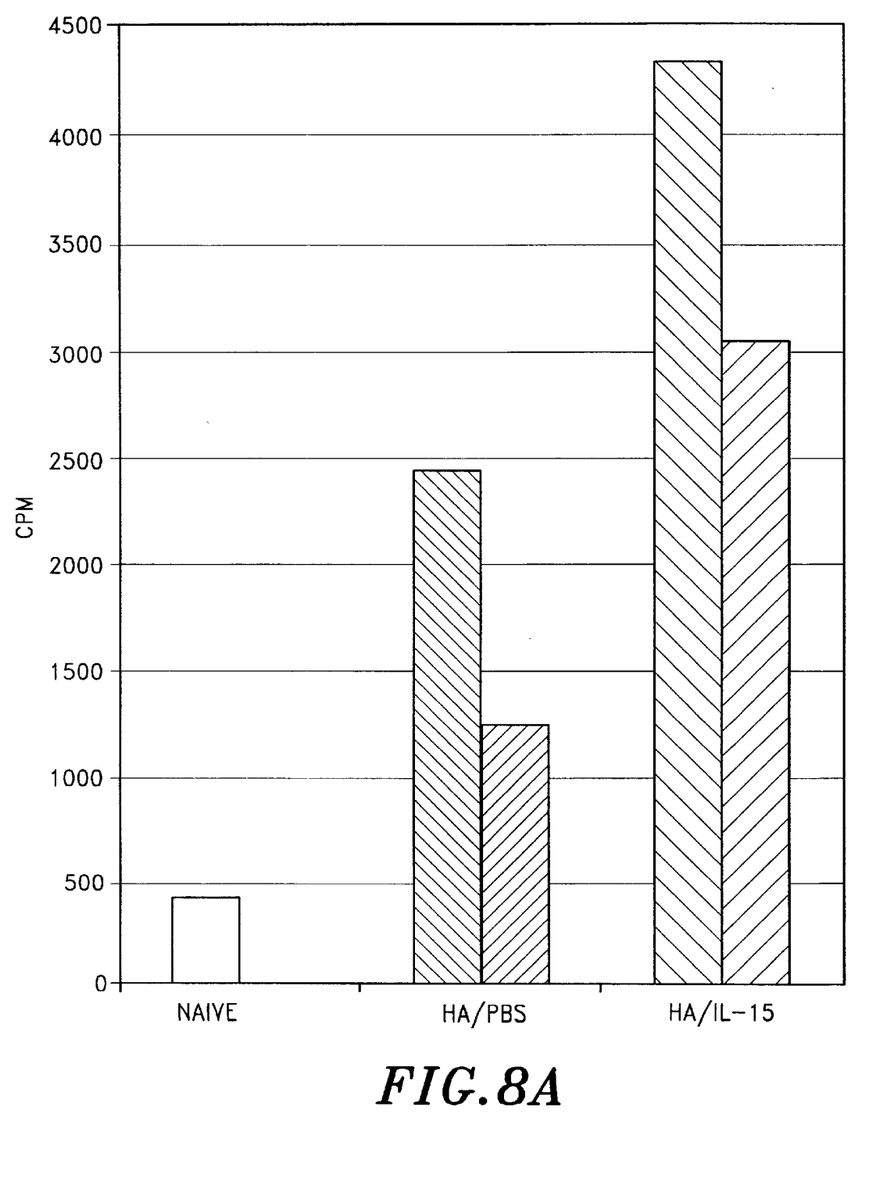
FIG. 8: In vivo administration of IL-15 during/after a primary antigenic challenge augments proliferative responsiveness of primed LN cells to a secondary antigenic challenge.
Figure 8B:
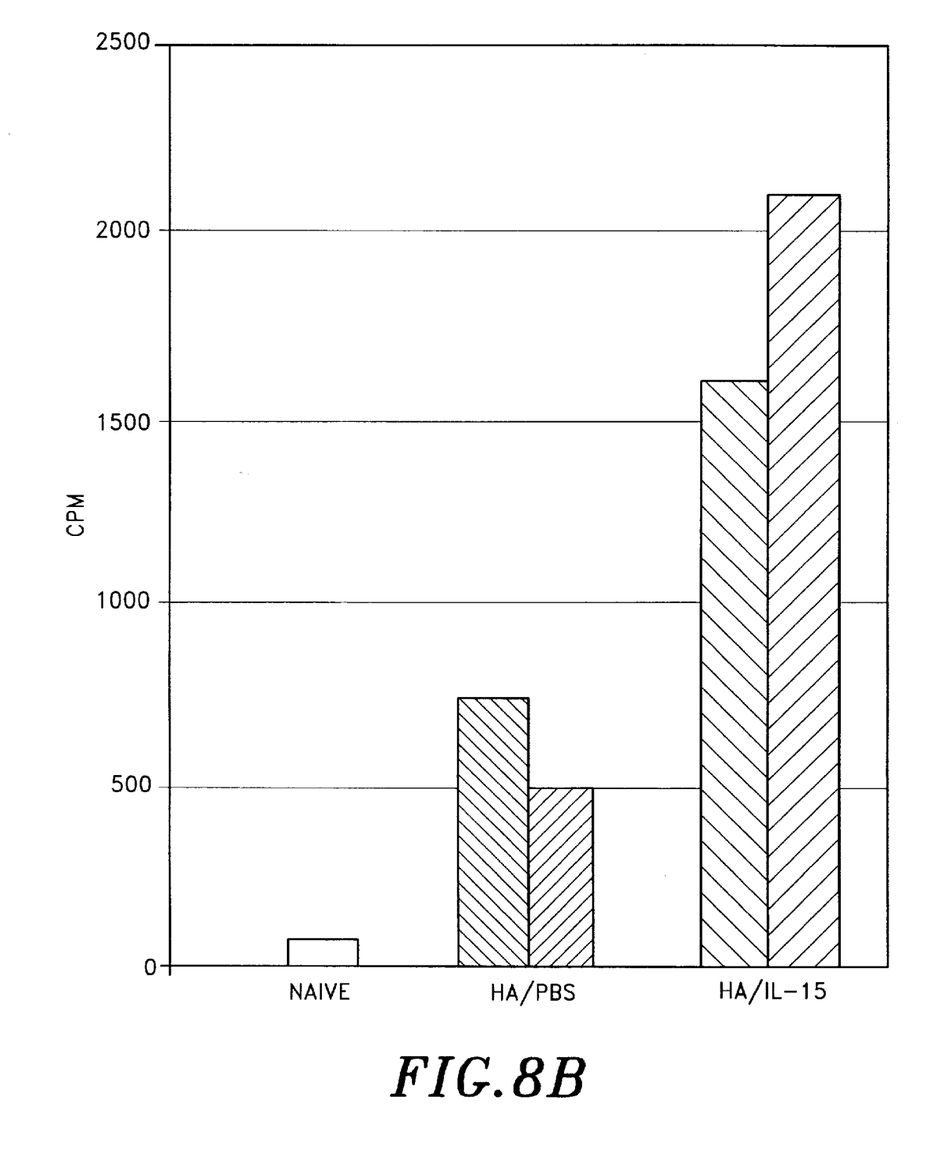
Figure 8C:
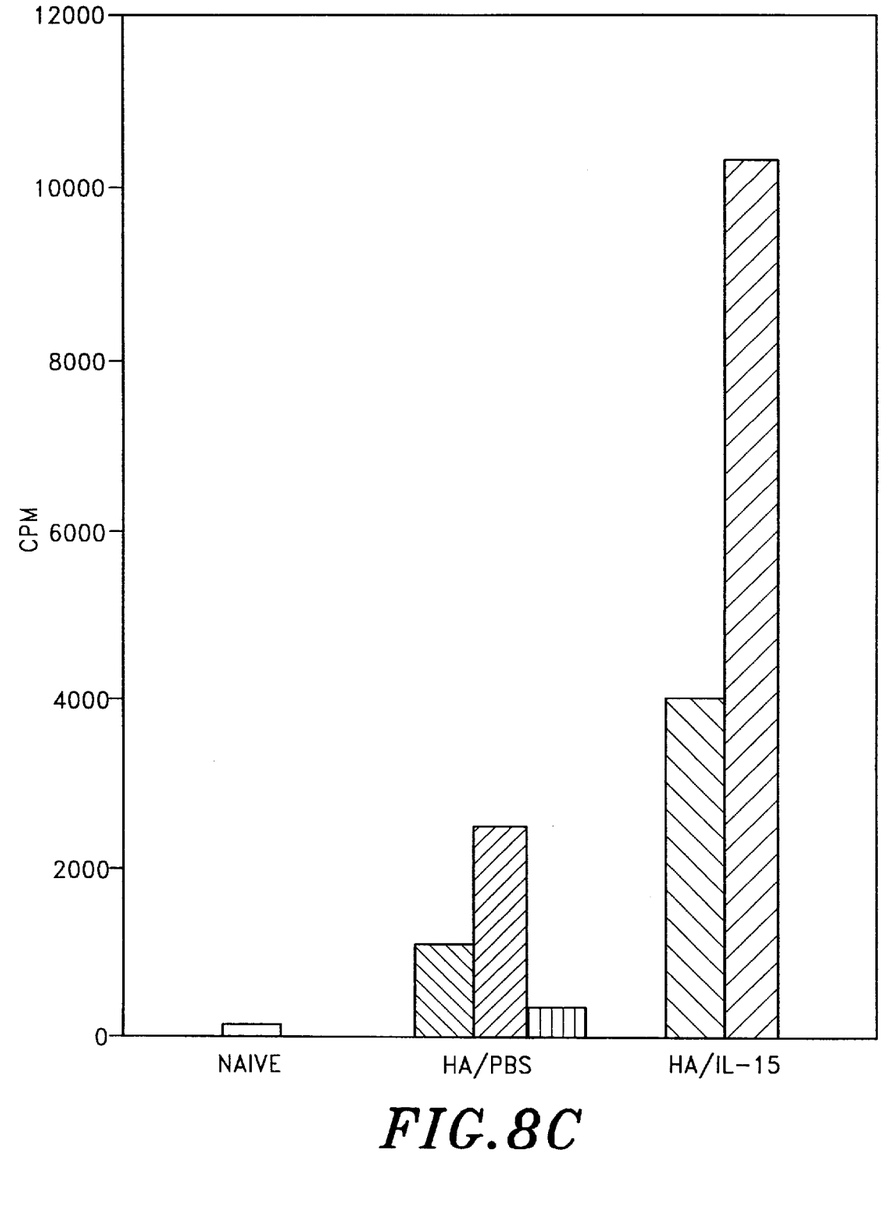

On day 21 after the first HA injection, mice were sacrificed and the draining lymph nodes (LN) of IL-15 or PBS-treated mice were isolated as well as LN from naive mice, LN cells were prepared and restimulated in vitro with 500 ng/ml HA or henn egg lysozyme (HEL) as an irrelevant antigen. Proliferation induced by these antigens was measured by $^3$H-thymidine incorporation. Results shown in FIG. 8 represent the specific proliferation against HA, i.e. cpm value obtained with HEL is subtracted from the absolute cpm value obtained with HA, from LN cells of two mice. Proliferation after 72 h (FIG. 8A) as well as 120 h (FIG. 8B) of LN cells from IL-15-treated mice was markedly increased, as compared to PBS-treated or naive mice. Also, addition of exogenous IL-15 during the restimulation period could prolong Ag-specific proliferative responses (FIG. 8C). Again, LN cells from IL-15-treated mice were most responsive to this exogenous IL-15.

The data demonstrate that slow-release delivery of IL-15 during and/or after a primary immune response results in an augmented proliferative responsiveness of cells from the draining LN against the immunizing antigen, indicative for the presence of a higher frequency of memory T cells in the immunized animal.

In a second experiment, mice were immunized with a single SC bolus injection of 2,5 µg HA (day 0) at the right flank and were treated, starting on day 4 after this initial immunization, with daily bolus injections of IL-15 for 10 consecutive days. The following doses were administered: day 4, 5 µg IL-15 ; day 5–7, 4 µg; day 8–10, 3 µg and day 11–13, 2 µg. The cytokine was injected SC at the same site as the Ag in a volume of 100 µl PBS. Control mice were injected with PBS without cytokine. On day 14, a new challenge of 2,5 µg HA was given to the IL-15- and PBS-treated mice, injected SC at the same site as the initial immunisation. Two weeks later, blood was collected by retro-orbital bleeding and serum was prepared immediately by incubating the blood samples at 37° C. for 20 minutes. Titers of antibody (Ab) directed against HA were determined by indirect ELISA.

Figure 9:
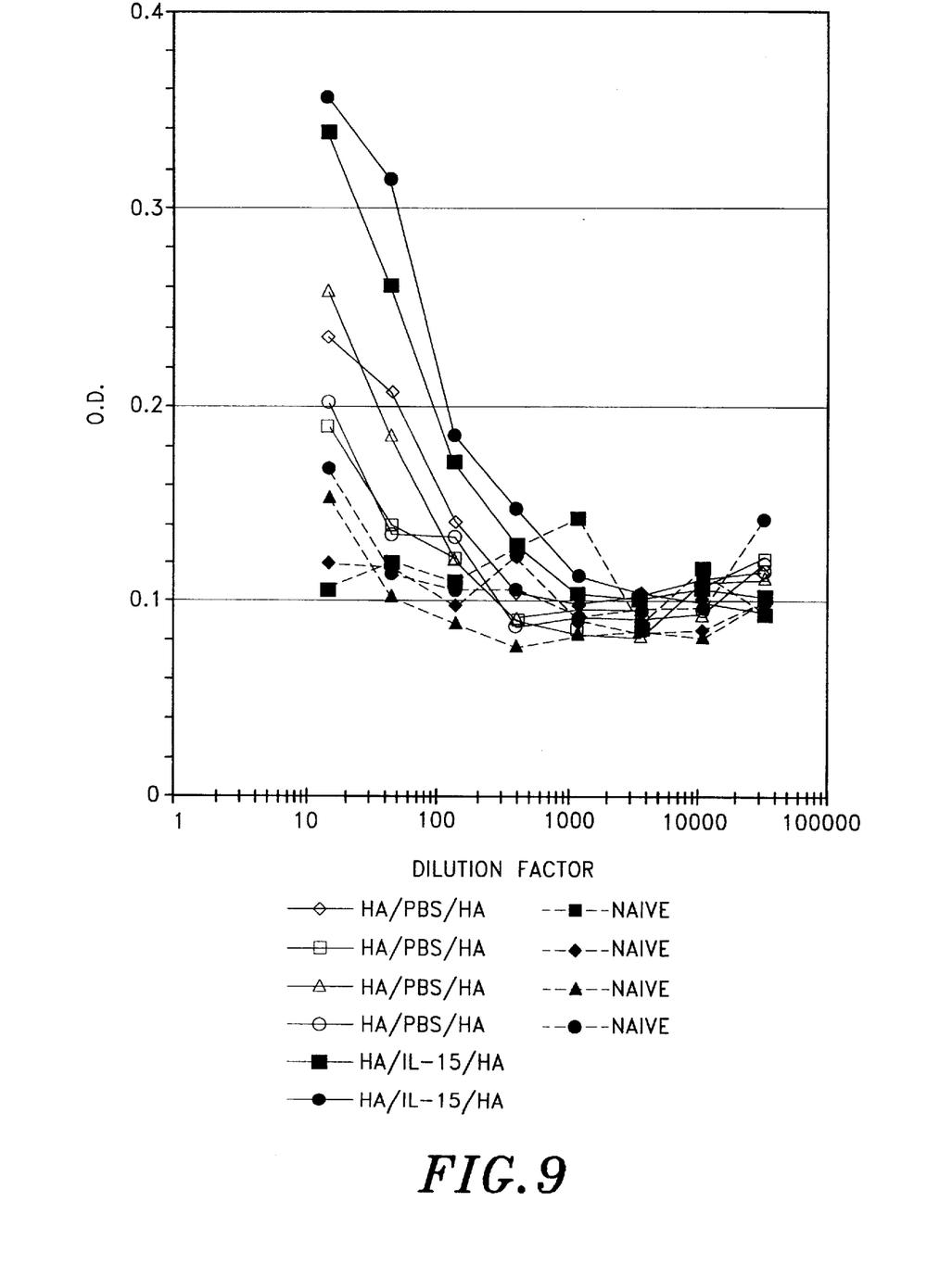
FIG. 9: In vivo administration of IL-15 during/after a primary antigenic challenge augments Ag-specific Ab titers elicited by a secondary antigenic challenge.

FIG. 9 demonstrates that the anti-HA Ab titer of the two IL-15-treated mice was enhanced, as compared to the four PBS treated mice. Titers in naive mice are shown as an additional control on ELISA background levels. The augmented anti-HA Ab titers are indicative that an enhanced immune response against the second HA challenge occurred in mice treated with IL-15 after the primary response. Taken together, it is shown that administration of IL-15 in vivo during and/or after an ongoing immune response enhances the secondary/memory response elicited by a renewed contact with the Ag involved.

| LIST OF ABBREVIATIONS | |
|---|---|
| aa | amino acid |
| Ab | antibody |
| Ag | antigen |
| AICD | activation-induced cell death |
| APC | antigen-presenting cell |
| BHA | bromelain cleaved haemagglutinin |
| IL | interleukin |
| LAK | lymphokine activated killer cell |
| 2-ME | β-mercaptoethanol |
| PBT | peripheral blood T lymphocytes |
| PHA | phytohaemagglutinin |
| TCR | T cell receptor |
| Th | T helper lymphocyte |
| cpm | count per minute |

Legends to the Figures

FIG. 1: IL-15 is mainly a survival factor, while IL-2 is mainly a proliferation-inducing factor.

T-HA cells were harvested on day 4 after antigenic restimulation, and were incubated in 200 µl containing the indicated concentrations of IL-2 or IL-15 for 72 h.

(A) $1 \times 10^4$ T-HA cells were cultured for 72 h with increasing concentrations of IL-2 or IL-15. Cultures were pulsed with $^3$H-thymidine for the last 8 h.

(B) Viable cell numbers in micro-cultures seeded with $2.10^4$ T-HA cells were determined on day 3 of culture by trypan-blue dye exclusion. Results shown are averages of 2 haemocytometer counts of 2 wells.

(C) % apoptotic cells in the source cultures was determined by flow cytometric quantitation of cells, which had taken up the exclusion dye PI.

FIG. 2: IL-15 induces a resting phenotype $2 \times 10^4$ T-HA cells were cultured with IL-2 (10 ng/ml) or IL-15 (1 ng/ml) for 48–72 h. Cell cycle status, cell size and expression of activation markers were analysed. (A) PI fluorescence intensity as a measure of cellular DNA content, and cell cycle distribution percentages. (B) forward light scatter as a measure of cell size. (C) (D) CD25 and CD71 expression. Dotted lines represent labeling with secondary Ab alone. (E) Rhodamine123 incorporation indicative for mitochondrial membrane potential values (MFI: mean fluorescence intensity).

FIG. 3: IL-15 or low-dose IL-2 treated T-HA cells show increased proliferation in response to Ag/APC stimulation.

T-HA lymphocytes were harvested on day 12 after antigenic restimulation and cultured for 48 h with the indicated concentrations of IL-2 or IL-15 in 24-well plates. Next, pretreated cells were harvested, cytokine was washed away and $1 \times 10^4$ cells were stimulated with $2 \times 10^5$ irradiated spleen cells as APC and 200 ng/ml purified BHA as antigen. $^3$H-thymidine was added for the last 12 h of the 84 h culture period. Data are expressed as cpm of $^3$H-thymidine incorporated.

FIG. 4: IL-15 or low-dose IL-2 treatment of T-HA cells results in increased generation of effector cells during an Ag/APC response.

T-HA lymphocytes were harvested on day 12 after antigenic restimulation and were pretreated for 48 h with IL-2 (7.7 ng/ml or 0.077 ng/ml) or IL-15 (1 ng/ml) followed by labelling with the green fluorescent membrane marker PKH2-GL. 12 h later, $1 \times 10^4$ labeled cells were stimulated with $2 \times 10^5$ irradiated spleen cells as APC and 200 ng/ml purified BHA as antigen. Cultures were harvested at the indicated time points and dead (A) and viable (B) cell numbers of the stained cell population were determined by flow cytometry and PI uptake, using the unlabeled spleen cells as an internal standard. Countings shown are averages of triplicate cultures.

FIG. 5: Culture of T-HA cells in the presence of IL-15 results both in optimal recovery of cells after primary antigenic restimulation and in optimal proliferative responsiveness upon secondary antigenic restimulation.

$1 \times 10^5$ T-HA lymphocytes, pretreated for 48 h with IL-2 (10 or 0.1 ng/ml) or IL-15 (1 ng/ml), were stimulated in 1 ml with $2 \times 10^6$ irradiated spleen cells and 200 ng/ml BHA. On day 4 these cultures were supplemented with the same concentrations of cytokine as during the pretreatment and incubated under these conditions for 8 more days.

(A) Viable cells were counted by trypan blue dye exclusion on day 12 after starting the antigenic restimulation described above. Data are represented as a cell recovery index, i.e. the factor by which the input cell number has multiplied on day 12.

(B) $1 \times 10^4$ of the recovered cells were stimulated a second time with Ag/APC and proliferation was determined by $^3$H-thymidine incorporation.

(C) The total proliferative response expected during the second antigenic restimulation is represented as a reactivity index, calculated as follows:

(cell recovery index described in FIG. 5(A))×(CPM measured on day 15 (FIG. 5(B))

FIG. 6: Culture of T-HA cells in the presence of IL-15 results in a strongly enhanced generation of immune effector cells.

Starting from day −2, T-HA lymphocytes were pretreated for 48 h with the indicated concentrations of IL-2 or IL-15. On day 0, $1 \times 10^5$ T-HA cells were stimulated in 1 ml with $2 \times 10^6$ irridated spleen cells and 200 ng/ml BHA. On day 4 these cultures were supplemented with the same concentrations of cytokine as during the pretreatment and incubated under these conditions for 8 more days. On day 12 after the first antigenic stimulation, $1 \times 10^4$ cells were restimulated with Ag/APC and the number of generated effectors was determined on day 15 as previously described. The total number of effector cells generated on day 15 per cell stimulated on day 0 is represented as a cell recovery index calculated as follows:

(number of cells harvested from the cultures on day 12)×(number of cells counted on day 15) $10^5 \times 10^4$ FIG. 7: IL-15 protects activated polyclonal CD4$^+$ T cell populations against growth factor withdrawal-induced PCD and TCR-induced death.

Freshly isolated, unsorted spleen cells from C57Bl/6 mice were polyclonally activated with soluble anti-CD3 mAb (1 μg/ml). On day 4, CD4$^+$ T cells were isolated by magnetic cell sorting and $7.5 \times 10^6$ cells were further cultured for 10 days without exogenously added cytokine or with addition of IL-15 (10 ng/ml) or IL-2 (10 ng/ml). On day 14 after the initial stimulation, cultures were harvested and survival, sensitivity for TCR-induced death and TCR-responsiveness were evaluated. (A) Viable CD4$^+$ T cell numbers were counted after addition of trypan blue. Survival is presented as the percentage recovery of the input cell numbers. 3 independent countings were performed, SD<15%. (B) Susceptibility for TCR-induced death was evaluated by restimulation of $1 \times 10^4$ viable IL-15- or IL-2-cultured cells, isolated by density gradient centrifugation, with plate-bound anti-CD3 mAb (10 μg/ml) for 24 h and determination of percentages of apoptotic CD4$^+$ T cells by PI uptake. Results represent 3 pooled wells. (C) Secondary responsiveness of activated CD4$^+$ T cell populations to appropriate TCR-stimulation was measured by restimulating $1 \times 10^4$ pretreated T lymphocytes with 1 μg/ml soluble anti-CD3 mAb and $2 \times 10^4$ IFN-γ-activated macrophages (Mf4/4), either in the absence or presence of 1 ng/ml IL-15 or IL-2. Naive CD4$^+$ T cells were added as a control to assure that these stimulation conditions could properly induce a proliferative response. Proliferation was measured by addition of $^3$H-thymidine for the last 12 h of the 84 h assay period. No proliferation could be detected in cultures of T cells and Mf4/4 without soluble anti-CD3 Ab (cpm<500) indicating that the observed response was strictly dependent on TCR triggering. Results represent means of triplicate cultures. Experiments on freshly isolated spleen cells were done 2 times with similar results.

FIG. 8: In vivo administration of IL-15 during/after a primary antigenic challenge augments proliferative reponsiveness of primed LN cells to a secondary antigenic challenge.

Mice were immunized with HA and treated for 14 days with IL-15 or PBS delivered by an ALZET mini-osmotic pump. On day 21 after the initial HA injection, mice were sacrificed and draining lymph nodes prepared. $2 \times 10^5$ LN cells were restimulated in 96-well microtiter plates with 500 ng/ml HA or HEL without exogenous cytokine. Results show the HA-specific proliferation, i.e. absolute HA-induced proliferation minus HEL-induced proliferation, of LN cell cultures from IL-15- (hatched) or PBS-treated (dotted) mice, measured by addition of $^3$H-thymidine after 72 h (A) or 120 h (B) for an additional 12 h. Data shown in (C) also represent HA-specific proliferation at 120 h but here 1 ng/ml exogenous IL-15 was added during the culture period. Each bar represents proliferation of LN cells derived from one individual mouse, except for the naive mice (black) where LN of three individuals were pooled.

FIG. 9: In vivo administration of IL-15 during/after a primary antigenic challenge augments Ag-specific Ab titers elicited by a secondary antigenic challenge.

Mice were immunized with HA and treated for 10 days with IL-15 or PBS delivered by daily bolus injections. One day after the last delivery, IL-15- or PBS-treated mice were rechallenged with HA. Two weeks later, blood samples were taken, sera prepared and anti-HA Ab detected with an indirect ELISA. The sera were serially diluted in Maxisorp 96-well plates (Nunc, Roskilde, Denmark) previously coated with HA by overnight incubation at 4° C. with 0,5 µg/ml stock solution of the Ag. Bound Ab was detected with goat anti-mouse IgG Ab (Sigma) using alkaline phosphatase-conjugated rabbit anti-goat IgG as detecting Ab (Sigma). Results are represented as O.D. values as a function of serum dilution factor. Each curve represents serum of an individual animal. Sera of naive mice were used as a control on background signals.

REFERENCES

1. Armitage R J et al. (1995) J Immunol 154(2): 483–90
2. Bamford R N et al. (1994) Proc Natl Acad Sci USA 91(11): 4940–4
3. Burton J D et al. (1994) Proc Natl Acad Sci USA 91(11): 4935–9
4. Carson W E et al. (1994) J Exp Med 180(4): 1395–403
5. Critchfield J M et al. in 'Apoptosis and the immune response', 1995, Wiley-Liss, Inc., New York; p. 55–114
6. Giri J G et al. (1995) EMBO J 14(15): 3654–63
7. Grabstein K H et al (1994) Science 264(5161): 965–8
8. Gray D (1993) Annu Rev Immunol 11: 49–77
9. Kanegane H & Tosato G (1996) Blood 88(1): 230–5
10. Khan I A & Kasper L H (1996) J Immunol 157: 2103–2108
11. Leclercq G et al. (1996) J Exp Med 184(2): 325–36
12. Lenardo M J (1991) Nature 353(6347): 858 61
13. Mueller D L et al. (1996) J Immunol 156(5): 1764–71
14. Nieto M et al. (1996) Eur J Immunol 26(6): 1302–7
15. Nishimura H et al. (1996) J Immunol 156(2): 663–9
16. Puzanov I J et al. (1996) J Immunol. 157: 4282–4285
17. Quinn L S et al. (1995) Endocrinology 136(8): 3669–72
18. Swain S L et al (1996) Immunological Reviews 150: 143–167
19. Tagaya Y et al. (1996) Immunity 4 (4): 329–36
20. Tamura T and Nariuchi, H (1992) J. Immunol. 148(8): 2370–2377
21. Wilkinson P C & Liew F Y (1995) J Exp Med. 181(3): 1255–9
22. Zhang X et al. (1995) J Exp Med 182(3): 699–709

What is claimed is:

1. A method of stimulating formation and promoting survival of memory T cells which recognize a specific antigen in a mammal in need thereof, comprising:
   administering IL-15 or active variants thereof capable of generating memory T-cells, wherein administration occurs after an ongoing immune response to said specific antigen to enhance the secondary/memory response elicited by a renewed contact with said antigen.

2. A method according to claim 1 for manipulating viability of memory cells generated after an ongoing immune response to said specific antigen and after clearance of said antigen.

3. A method according to claim 1 for manipulating responsiveness of memory cells to a new encounter with antigen.

4. A method according to claim 1, wherein responsiveness towards renewed antigen challenge of said memory cells is enhanced.

5. A method according to claim 1 for protecting ex vivo propagated T lymphocytes against cells death in absence of growth factor.

6. A method according to claim 1, wherein the memory cells are CD4$^+$ T lymphocytes.

7. A pharmaceutical composition comprising ex vivo cultivated T lymphocytes, treated with IL-15 or active variants thereof, during the ex vivo cultivation procedure.

* * * * *